(12) United States Patent
Broden

(10) Patent No.: US 7,115,118 B2
(45) Date of Patent: Oct. 3, 2006

(54) IMPLANTABLE PRESSURE-ACTIVATED MICRO-VALVE

(75) Inventor: David A. Broden, Andover, MN (US)

(73) Assignee: Rosemount Inc., Eden Prairie, MN (US)

( * ) Notice: Subject to any disclaimer, the term of this patent is extended or adjusted under 35 U.S.C. 154(b) by 396 days.

(21) Appl. No.: 10/408,743

(22) Filed: Apr. 7, 2003

(65) Prior Publication Data

US 2003/0229337 A1 Dec. 11, 2003

Related U.S. Application Data

(60) Provisional application No. 60/370,819, filed on Apr. 8, 2002.

(51) Int. Cl.
*A61K 9/22* (2006.01)

(52) U.S. Cl. .................... 604/891.1; 604/237

(58) Field of Classification Search ........... 604/890.1, 604/6.1, 33, 34, 237, 892.1, 891.1, 288.01, 604/288.02, 288.03, 288.04, 31, 32
See application file for complete search history.

(56) References Cited

U.S. PATENT DOCUMENTS

| | | | | |
|---|---|---|---|---|
| 4,152,098 A | | 5/1979 | Moody et al. ............. 417/413 |
| 4,505,710 A | * | 3/1985 | Collins .................... 604/891.1 |
| 4,604,090 A | | 8/1986 | Reinicke .................... 604/118 |
| 4,760,837 A | * | 8/1988 | Petit ........................ 604/891.1 |
| 4,776,838 A | | 10/1988 | Sainte-Rose et al. ......... 604/9 |
| 4,840,615 A | * | 6/1989 | Hancock et al. ........ 604/288.02 |
| 5,062,841 A | * | 11/1991 | Siegel ..................... 604/891.1 |
| 5,085,656 A | * | 2/1992 | Polaschegg .............. 604/891.1 |
| 5,219,278 A | | 6/1993 | van Lintel .................. 417/413 |
| 5,308,348 A | | 5/1994 | Balaban et al. .......... 604/892.1 |
| 5,807,303 A | * | 9/1998 | Bays ............................ 604/9 |
| 6,048,328 A | * | 4/2000 | Haller et al. ........... 604/288.03 |
| 6,240,962 B1 | * | 6/2001 | Tai et al. .................... 137/859 |
| 6,273,117 B1 | * | 8/2001 | McPhee ....................... 137/12 |
| 6,283,949 B1 | * | 9/2001 | Roorda .................. 604/288.02 |
| 2001/0022350 A1 | * | 9/2001 | Ito ............................... 251/65 |
| 2002/0013545 A1 | * | 1/2002 | Soltanpour et al. ............ 604/9 |
| 2002/0029814 A1 | * | 3/2002 | Unger et al. ................. 137/824 |

FOREIGN PATENT DOCUMENTS

| | | | |
|---|---|---|---|
| DE | 41 40 251 A 1 | 6/1993 | |
| EP | 0 951 916 A 2 | 10/1999 | .................. 5/142 |
| EP | 0 951 916 A 3 | 10/1999 | .................. 5/142 |
| GB | 2 243 777 A | 11/1991 | |
| WO | WO 00/61215 | 10/2000 | |

* cited by examiner

Primary Examiner—Nicholas D. Lucchesi
Assistant Examiner—Laura A. Bouchelle
(74) Attorney, Agent, or Firm—Westman, Champlin & Kelly, P.A.

(57) ABSTRACT

An implantable pressure-activated microvalve is disclosed. The valve includes a chamber that can be coupled to an external reservoir. A deflectable diaphragm is fluidically coupled to the chamber and arranged such that pressure of an in vivo fluid will bear against the deflectable diaphragm. When the pressure exceeds a selected threshold, the diaphragm deflects and allows material within the chamber to mix with the in vivo fluid.

12 Claims, 3 Drawing Sheets

IMPLANTABLE PRESSURE-ACTIVATED MICRO-VALVE

BACKGROUND OF THE INVENTION

This application claims the priority of an earlier filed co-pending provisional Patent Application Serial No. 60/370,819, filed Apr. 8, 2002 entitled IMPLANTABLE PRESSURE-ACTIVATED MICROVALVE.

Current medical treatments are aided by a vast array of methods and devices for delivering substances, such as medicines, to a patient. One example of such systems is the implantable drug delivery system. However, generally, most implantable drug delivery systems are relatively complex and costly. Usually the cost of such systems is tolerated because implantable drug delivery is of such importance and/or convenience. However, a device and method that could provide at least some of the benefits of implantable drug delivery with significantly reduced costs would benefit patients.

SUMMARY OF THE INVENTION

An implantable pressure-activated microvalve is disclosed. The valve includes a chamber that can be coupled to an external reservoir. A deflectable diaphragm is fluidically coupled to the chamber and arranged such that pressure of an in vivo fluid will bear against the deflectable diaphragm. When the pressure exceeds a selected threshold, the diaphragm deflects and allows material within the chamber to mix with the in vivo fluid.

DETAILED DESCRIPTION OF THE PREFERRED EMBODIMENTS

Embodiments of the present invention include a simple implantable pressure-activated micro-valve that is adapted for in vivo use and can selectively provide a substance, such as a medicine, in response to a pressure of a body fluid, such as blood, reaching a selected threshold. It is anticipated that embodiments of the present invention will be useful for control of elevated blood pressure. For example, drugs that treat such conditions can be dispensed in direct response to a pressure signal of the blood itself. It is believed that such drug delivery can help ameliorate short term "pressure spikes" in blood pressure.

Although aspects of the present invention will be described with respect to dispensing blood pressure lowering drugs, any suitable medicines or substances can be used in response to any in vivo fluid pressure. In accordance with some aspects, additional medicines, or other suitable substances are stored in a reservoir that can be disposed outside the body. Preferably, the valve itself is constructed from microelectromechanical systems (MEMS) based materials which are generally compatible with in vivo operation. Examples of such materials include, but are not limited to silicon, Sapphire, ceramic, and other known bio-compatible materials. Metals such as titanium can also be used. Further, the pressure valve itself is preferably sized such that it can be implanted through a hypodermic needle. In accordance with aspects of the invention, the pressure valve is all mechanical and highly reliable. Further, a diaphragm of the pressure valve can be designed to allow a very accurate range of opening pressures. Examples of such pressures can include 180, 200, 220 Torr. As will be appreciated, the pressure-activated micro-valve will respond as needed, thus closing or generally ceasing dispensation when the pressure passes below the selected threshold. The valve itself is anticipated to be extremely inexpensive such that it can be used for disposable applications.

Figure 1:
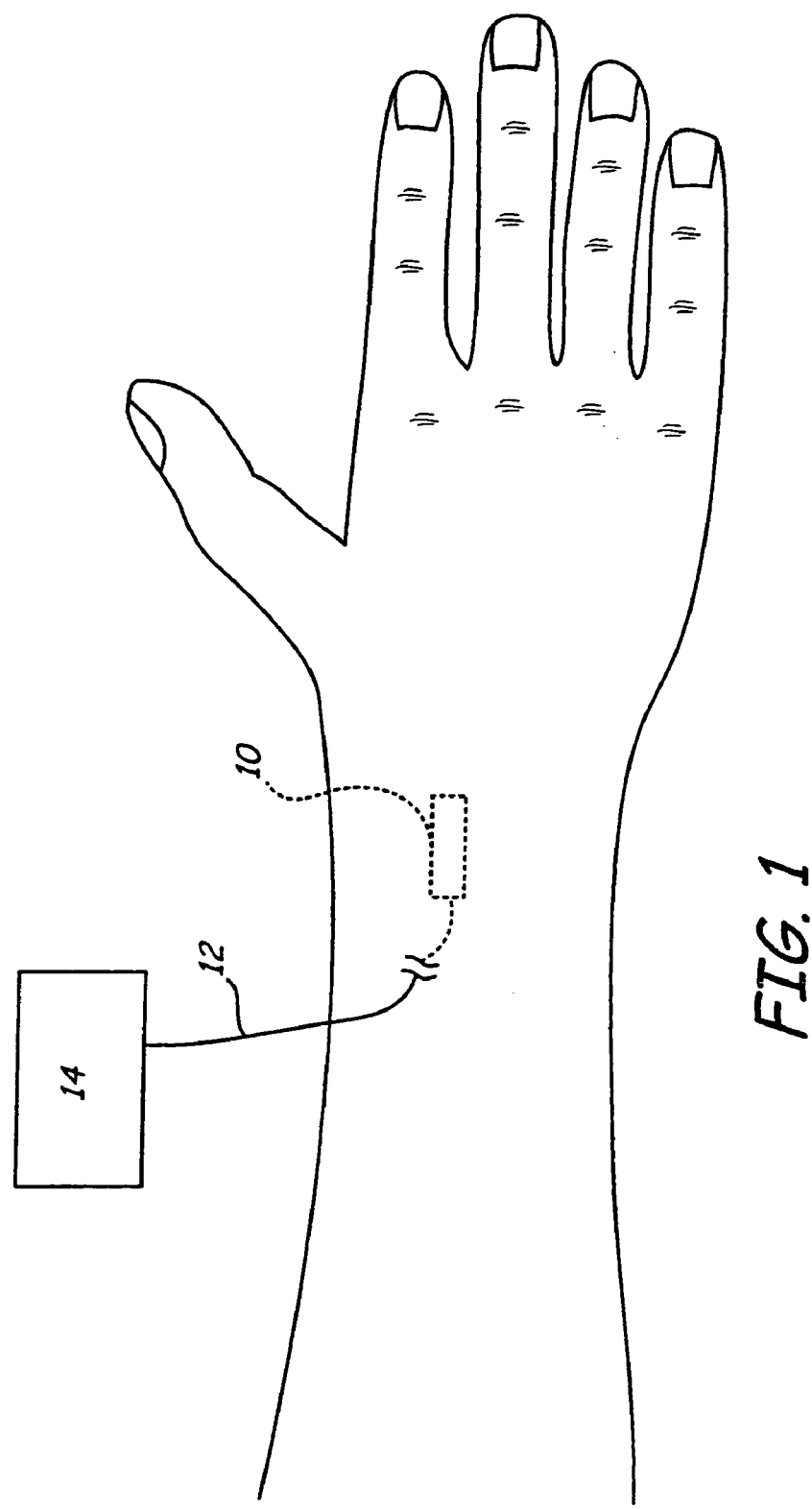
FIG. 1 is a diagrammatic view of pressure-activated micro-valve 10 implanted within a patient in accordance with an embodiment of the present invention.

FIG. 1 is a diagrammatic view of pressure-activated micro-valve 10 implanted within a patient. In accordance with one aspect of the present invention, micro-valve 10 is fluidically coupled, via line 12, to external reservoir 14.

Figure 2:
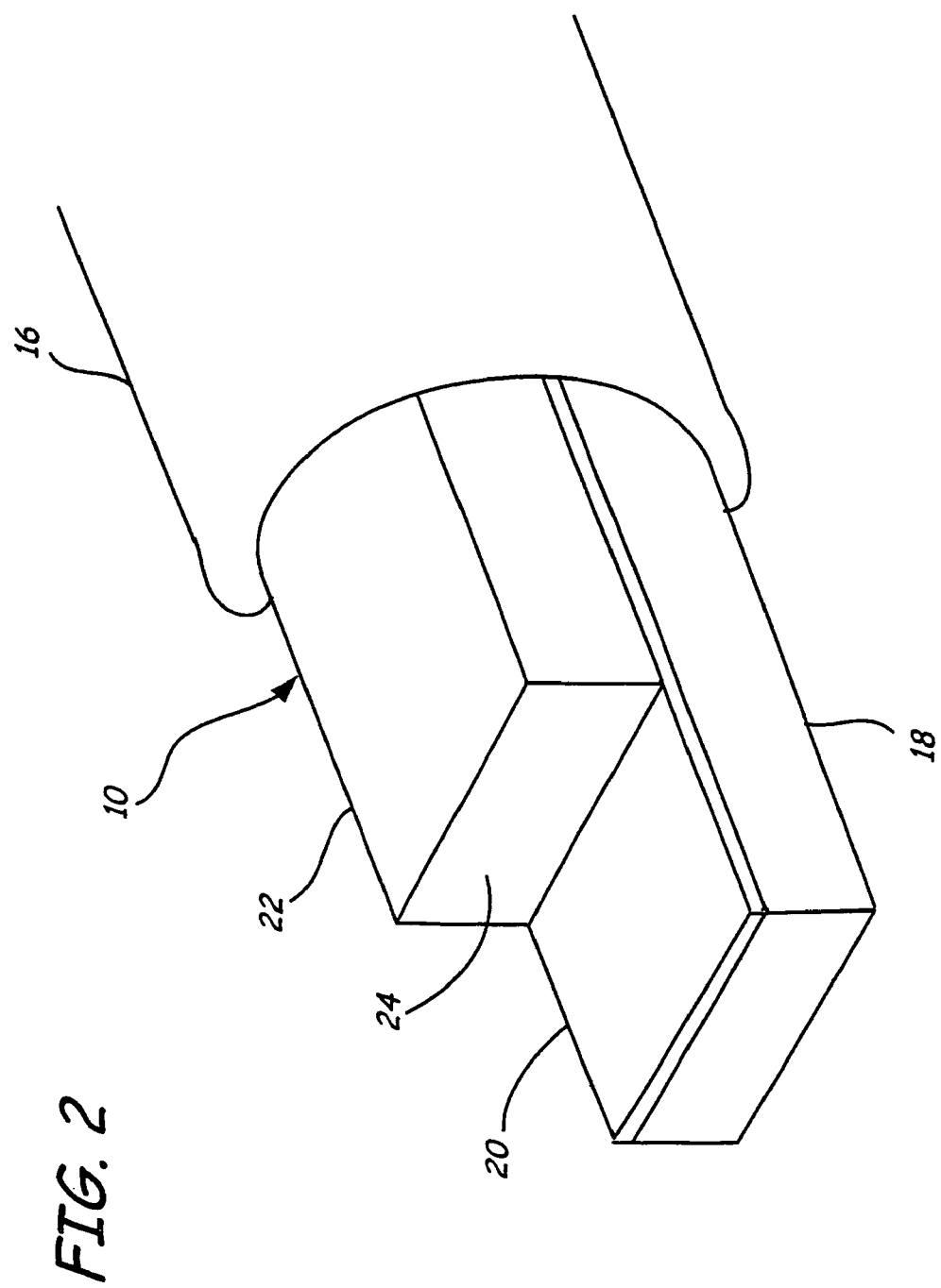
FIG. 2 is an enlarged perspective view of a pressure activated micro-valve in accordance with an embodiment of the invention.

FIG. 2 is an enlarged perspective view of valve 10. Preferably, valve 10 is disposed within stainless steel sheath 16 which facilitates introduction of valve 10 into the body. Valve 10 is generally constructed from a sandwich of MEMs materials. Valve 10 includes bottom layer 18, deflectable diaphragm 20 and top layer 22 bonded together in accordance with known techniques. Bottom layer 18 includes a recess allowing deflectable diaphragm 20 to deflect therein, while top layer 22 includes a chamber 28 that provides the desired material when diaphragm 20 deflects. Those skilled in the art will recognize that this geometry may be reversed without departing from the spirit and scope of the invention. Thus, more generally, a first layer includes a recess for diaphragm deflection, while the second layer includes the chamber for the selected pharmaceutical material.

The materials selected for bottom layer 18, deflectable diaphragm 20, and top layer 22 are preferably materials such as silicon, Sapphire and ceramic. While it is preferable that all such layers are the same material, they need not be.

Figure 3A:
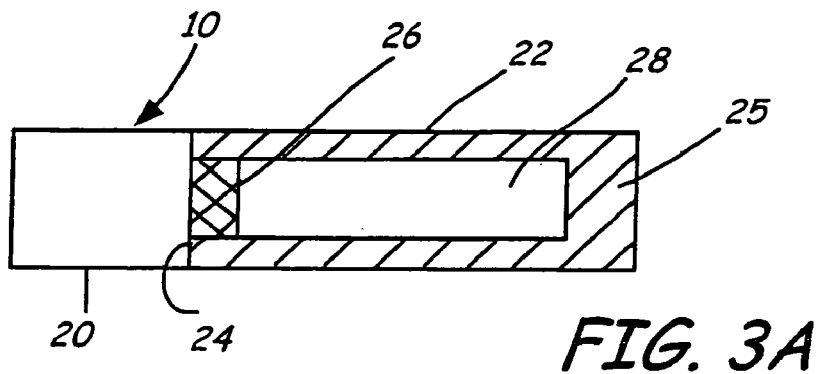
FIG. 3A is a top plan view of valve 10 in accordance with an embodiment of the present invention.

FIG. 3A is a top plan view of valve 10. Deflectable diaphragm 20 can be seen extending beyond edge 24 of top layer 22. Top layer 22 is bonded to deflectable diaphragm 22 at area 25, but not at area 26. The portion of diaphragm 20 proximate edge 24 is deflectable such that when pressurized with sufficient pressure, diaphragm 20 deflects in the area of crosshatching 26 to allow the contents of chamber 28 to pass therethrough.

Figure 3B:
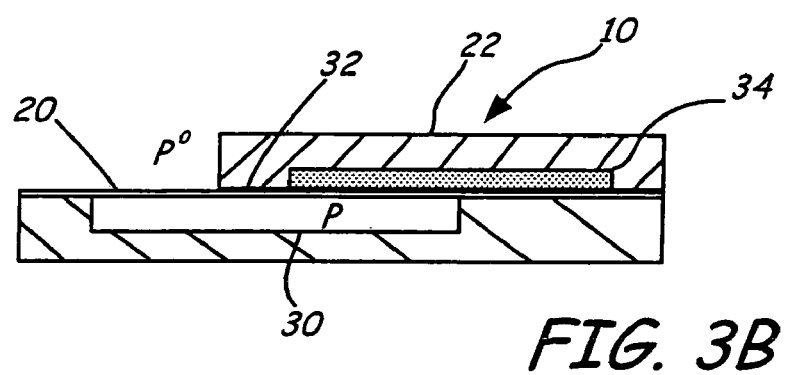
FIG. 3B is a side elevation cross-section view of valve 10 in a "closed" state in accordance with an embodiment of the present invention.

FIG. 3B is a side elevation cross-section view of valve 10 in a "closed" state. In this state, valve 10 is subjected to an external pressure of $P^0$. A region 30 below diaphragm 20 is pressurized to pressure P. When the difference between pressure $P^0$ and pressure P exceeds the preloaded sealing force of deflectable diaphragm 20, diaphragm 20 itself will deflect away from surface 32 of top layer 22 thereby allowing contents 34 within chamber 28 to be dispensed.

Figure 3C:
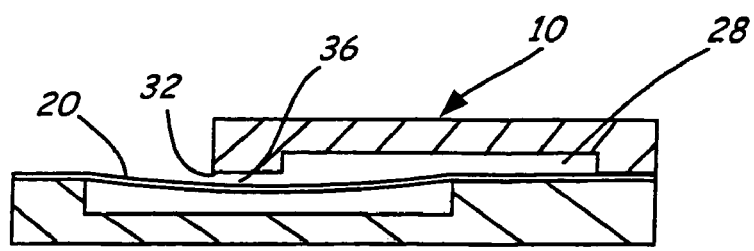
FIG. 3C is side elevation cross-section view of valve 10 in the open or dispensing state in accordance with an embodiment of the present invention.

FIG. 3C is side elevation cross-section view of valve 10 in the dispensing state. FIG. 3C shows deflectable diaphragm 20 deflected from surface 32 to generate gap 36 allowing contents of chamber 28 to pass therethrough.

Although the present invention has been described with reference to preferred embodiments, workers skilled in the art will recognize that changes may be made in form and detail without departing from the spirit and scope of the invention.

What is claimed is:

1. An implantable pressure actuated valve comprising:
   a first layer having a recess therein;
   a deflectable diaphragm bonded to the first layer and having a deflectable portion disposed to deflect into the recess;
   a second layer partially bonded to the deflectable diaphragm and having a chamber therein, wherein the chamber is in fluidic communication with the diaphragm;
   wherein the diaphragm is configured to deflects into the recess, in response to pressure of a body fluid, and wherein during diaphragm deflection at least a portion of the chamber is open to release a material.

2. The valve of claim 1, wherein the first layer is a bottom layer.

3. The valve of claim 1, wherein the second layer is a top layer.

4. The valve of claim 1, wherein the first layer, deflectable diaphragm and second layer are formed of the same material.

5. The valve of claim 1, wherein at least one of the first layer, second layer and deflectable diaphragm are formed from ceramic.

6. The valve of claim 1, wherein at least one of the first layer, second layer and deflectable diaphragm are formed from silicon.

7. The valve of claim 1, wherein at least one of the first layer, second layer and deflectable diaphragm are formed from sapphire.

8. The valve of claim 1, wherein the diaphragm is constructed to deflect at a selected pressure.

9. The valve of claim 1, wherein the chamber is coupleable to an external reservoir.

10. The valve of claim 1, wherein the material in the chamber includes a pharmaceutical substance.

11. The valve of claim 1, wherein at least one of the first layer, second layer and deflectable diaphragm are formed of metal.

12. The valve of claim 11, wherein the metal is titanium.

* * * * *

UNITED STATES PATENT AND TRADEMARK OFFICE
CERTIFICATE OF CORRECTION

PATENT NO. : 7,115,118 B2 Page 1 of 1
APPLICATION NO. : 10/408743
DATED : October 3, 2006
INVENTOR(S) : Broden It is certified that error appears in the above-identified patent and that said Letters Patent is hereby corrected as shown below:

What is claimed is:

In column 3, lines 14-15:

"wherein the diaphragm is configured to deflects into the recess, in response to pressure of a body"

should read:

-- wherein the diaphragm is configured to deflect into the recess in response to pressure of a body --

Signed and Sealed this

Fourth Day of March, 2008

JON W. DUDAS
*Director of the United States Patent and Trademark Office*